US008912239B2

(12) United States Patent
McAlister

(10) Patent No.: US 8,912,239 B2
(45) Date of Patent: Dec. 16, 2014

(54) CARBON RECYCLING AND REINVESTMENT USING THERMOCHEMICAL REGENERATION

(75) Inventor: Roy Edward McAlister, Phoenix, AZ (US)

(73) Assignee: McAlister Technologies, LLC, Phoenix, AZ (US)

(*) Notice: Subject to any disclaimer, the term of this patent is extended or adjusted under 35 U.S.C. 154(b) by 13 days.

(21) Appl. No.: 13/027,196

(22) Filed: Feb. 14, 2011

(65) Prior Publication Data

US 2011/0201698 A1 Aug. 18, 2011

Related U.S. Application Data

(60) Provisional application No. 61/304,403, filed on Feb. 13, 2010.

(51) Int. Cl.
| | | |
|---|---|---|
| C10L 1/02 | (2006.01) | |
| C01B 3/24 | (2006.01) | |
| B01J 19/12 | (2006.01) | |
| B01J 19/18 | (2006.01) | |
| B01J 19/20 | (2006.01) | |
| F24J 2/07 | (2006.01) | |
| G01N 35/00 | (2006.01) | |
| G01N 1/40 | (2006.01) | |
| G01N 1/02 | (2006.01) | |

(52) U.S. Cl.
CPC ............... *C01B 3/24* (2013.01); *B01J 19/127* (2013.01); *B01J 19/1812* (2013.01); *B01J 19/20* (2013.01); *F24J 2/07* (2013.01); *G01N 35/00871* (2013.01); *B01J 2219/00085* (2013.01); *B01J 2219/187* (2013.01); *C01B 2203/0266* (2013.01); *C01B 2203/04* (2013.01); *C01B 2203/0465* (2013.01); *C01B 2203/0485* (2013.01); *C01B 2203/0811* (2013.01); *C01B 2203/0822* (2013.01); *C01B 2203/0872* (2013.01); *C01B 2203/0883* (2013.01); *G01N 1/405* (2013.01); *G01N 35/00613* (2013.01); *G01N 2001/021* (2013.01); *Y02E 60/366* (2013.01); *Y02E 10/41* (2013.01); *Y02E 60/364* (2013.01); *C10J 2300/0909* (2013.01); *C10J 2300/1656* (2013.01); *C10J 2300/1665* (2013.01)
USPC .......................................... 518/700; 518/702

(58) Field of Classification Search
USPC .................................................. 518/700, 702
See application file for complete search history.

(56) References Cited

U.S. PATENT DOCUMENTS

| 2,180,626 | A | * | 11/1939 | Delorme .................... 530/360 |
| 4,339,546 | A | | 7/1982 | Randalls |

(Continued)

FOREIGN PATENT DOCUMENTS

| JP | 2005-289856 A | 10/2005 |
| JP | 2007-314745 A | 12/2007 |

(Continued)

OTHER PUBLICATIONS

"Geologic Sequestration of Carbon Dioxide | UIC | US EPA." US Environmental Protection Agency. Accessed: Aug. 30, 2009. <http://www.epa.gov/safewater/uic/wells_sequestration.html>. pp. 1-5.

(Continued)

*Primary Examiner* — Rosalynd Keys
(74) *Attorney, Agent, or Firm* — Perkins Coie LLP

(57) ABSTRACT

Techniques, systems, apparatus and material are disclosed for regeneration or recycling of carbon dioxide into renewable liquid fuel. In one aspect, a method of recycling carbon to produce a renewable fuel can include harvesting carbon dioxide emitted from an industrial process. Biomass waste is dissociated under an anaerobic reaction to produce hydrogen. The harvested carbon dioxide is reacted with the biomass waste produced hydrogen under pressure and heat to generate a renewable fuel.

14 Claims, 8 Drawing Sheets

(56) References Cited

U.S. PATENT DOCUMENTS

| | | | |
|---|---|---|---|
| 4,787,321 | A | 11/1988 | Schnellbacher et al. |
| 5,343,699 | A | 9/1994 | McAlister |
| 5,882,484 | A | 3/1999 | Pyy |
| 6,024,032 | A | 2/2000 | Sharpe |
| 6,133,328 | A | 10/2000 | Lightner |
| 6,155,212 | A | 12/2000 | McAlister |
| 6,270,731 | B1 | 8/2001 | Kato et al. |
| 6,446,597 | B1 | 9/2002 | McAlister |
| 6,890,419 | B2 | 5/2005 | Reichman et al. |
| 7,033,570 | B2 | 4/2006 | Weimer et al. |
| 7,033,822 | B2 | 4/2006 | Maston |
| 7,132,090 | B2 | 11/2006 | Dziedzic et al. |
| 7,138,046 | B2 | 11/2006 | Roychowdhury |
| 7,169,821 | B2 | 1/2007 | Branson |
| 7,309,435 | B2 | 12/2007 | Rozich |
| 7,425,315 | B2 | 9/2008 | Kruesi |
| 7,482,078 | B2 | 1/2009 | Sridhar et al. |
| 7,491,453 | B2 | 2/2009 | Logan et al. |
| 7,507,341 | B2 | 3/2009 | Gallagher et al. |
| 7,562,708 | B2 | 7/2009 | Cogliandro et al. |
| 7,569,203 | B2 | 8/2009 | Fridman et al. |
| 7,572,369 | B2 | 8/2009 | Gallagher et al. |
| 7,572,530 | B2 | 8/2009 | Gottmann et al. |
| 7,575,822 | B2 | 8/2009 | Mitlitsky et al. |
| 7,591,880 | B2 | 9/2009 | Levan et al. |
| 7,599,760 | B2 | 10/2009 | Dutta et al. |
| 7,618,606 | B2 | 11/2009 | Fan et al. |
| 7,628,137 | B1 | 12/2009 | McAlister |
| 7,878,131 | B2 | 2/2011 | Becchetti et al. |
| 7,906,559 | B2 | 3/2011 | Olah et al. |
| 7,931,997 | B2 | 4/2011 | Gottmann et al. |
| 7,947,155 | B1 | 5/2011 | Green et al. |
| 8,022,260 | B2 | 9/2011 | O'Connor et al. |
| 8,070,835 | B2 | 12/2011 | McAlister |
| 8,212,088 | B2 | 7/2012 | Olah et al. |
| 8,226,798 | B2 | 7/2012 | Van Aardt et al. |
| 8,318,997 | B2 | 11/2012 | McAlister |
| 2002/0077401 | A1* | 6/2002 | Chaudhary et al. ........... 524/394 |
| 2004/0253168 | A1 | 12/2004 | Chu |
| 2006/0280669 | A1 | 12/2006 | Jones |
| 2007/0056842 | A1 | 3/2007 | Roychowdhury |
| 2007/0099038 | A1 | 5/2007 | Galloway |
| 2007/0298478 | A1* | 12/2007 | Offerman et al. ............. 435/167 |
| 2008/0128259 | A1 | 6/2008 | Kostek et al. |
| 2008/0233029 | A1 | 9/2008 | Fan et al. |
| 2008/0264771 | A1 | 10/2008 | Dam-Johansen et al. |
| 2009/0007484 | A1 | 1/2009 | Smith |
| 2009/0183430 | A1 | 7/2009 | Schubert et al. |
| 2009/0202413 | A1 | 8/2009 | Saxena |
| 2009/0208784 | A1 | 8/2009 | Perry et al. |
| 2009/0208785 | A1 | 8/2009 | McElroy |
| 2009/0246596 | A1 | 10/2009 | Sridhar et al. |
| 2009/0269626 | A1 | 10/2009 | Mitlitsky et al. |
| 2009/0273240 | A1 | 11/2009 | Gurunathan et al. |
| 2009/0280360 | A1 | 11/2009 | Weingaertner et al. |
| 2009/0291346 | A1 | 11/2009 | Hickey et al. |
| 2010/0275823 | A1 | 11/2010 | Pahls |
| 2010/0298450 | A1 | 11/2010 | Datta et al. |
| 2011/0036320 | A1 | 2/2011 | Peret |
| 2011/0070510 | A1 | 3/2011 | McAlister |

FOREIGN PATENT DOCUMENTS

| | | |
|---|---|---|
| JP | 2010-031187 A | 2/2010 |
| WO | WO-2005021474 A1 | 3/2005 |
| WO | WO-2007122498 A2 | 11/2007 |
| WO | WO-2009-002191 A2 | 12/2008 |
| WO | WO-2011031752 A2 | 3/2011 |
| WO | WO-2011100695 A2 | 8/2011 |

OTHER PUBLICATIONS

"NETL: What Is Carbon Sequestration?" US Department of Energy—National Energy Technology Laboratory. Accessed: Aug. 30, 2009. <http://www.netl.doe.gov/technologies/carbon_swq/FAQs/carbon-carbon-seq.html>, pp. 1-5.

"US EPA—Carbon Sequestration in Agriculture and Forestry: Frequently Asked Questions," US Environmental Protection Agency. Published: Oct. 19, 2006. Accessed: Aug. 30, 2009. <http://www.epa.gov/sequestration/faq.html>, pp. 1-5.

Coils, Alison. "Carbon Sequestration." Environmental Change Institute. Accessed: Aug. 30, 2009. <http://climatex.org/articles/climate-change-info/carbon-sequestration/>. pp. 1-4.

Richard, Michael Graham. "Important! Why Carbon Sequestration Won't Save Us." TreeHugger. Published: Jul. 31, 2006. <http://treehugger.com/files/2006/07/carbon_sequestration.php>. pp. 1-6.

Salleh, Anna. "Urea 'Climate Solution' May Backfire." ABC.net.au. Published: Nov. 9, 2007. Accessed: Aug. 30, 2009. <http://www.abc.net.au/science/articles/2007/11/09/2085584.htm>. pp. 1-3.

International Search Report and Written Opinion for PCT Application No. PCT/US2011/024771; Applicant: McAlister Technologies, LLC; Date of Mailing: Feb. 14, 2011; 8 pages.

International Search Report and Written Opinion for PCT Application No. PCT/US2011/024801; Applicant: McAlister Technologies, LLC; Date of Mailing: Oct. 31, 2011; 10 pages.

International Search Report and Written Opinion for PCT Application No. PCT/US2011/024800; Applicant: McAlister Technologies, LLC; Date of Mailing: Oct. 20, 2011; 12 pages.

International Search Report and Written Opinion for PCT Application No. PCT/US2012/050619; Applicant McAlister Technologies, LLC; Date of Mailing: Feb. 13, 2013; 16 pages.

European Search Report for Application 11742987.8; Report Dated Feb. 19, 2014; 6 pages.

Bill, Alain, Carbon Dioxide Hydrogenation to Methanol at Low Pressure and Temperature, Ecole Polytechnique Federale De Lausanne, 1998, Thesis No. 1726. pp. 1-3, 9, 10, 23, 48.

* cited by examiner

CARBON RECYCLING AND REINVESTMENT USING THERMOCHEMICAL REGENERATION

CLAIM OF PRIORITY

The present application claims priority to and the benefit of U.S. Patent Application No. 61/304,403, filed on Feb. 13, 2010 and titled FULL SPECTRUM ENERGY AND RESOURCE INDEPENDENCE, which is incorporated herein by reference in its entirety. To the extent the foregoing application and/or any other materials incorporated herein by reference conflict with the disclosure presented herein, the disclosure herein controls.

BACKGROUND

This application relates to devices, techniques and materials related to thermochemical regeneration of carbon dioxide into liquid fuel.

The Industrial Revolution has produced the infrastructure, mechanized equipment, appliances, and communications systems to stimulate civilization's 7 billion people to burn more than one million years of fossil coal, oil, natural gas, and shale accumulations each year.

Global-scale participation in the Industrial Revolution has produced interrelated problems of finite resource depletion and economic inflation; loss of productivity due to diseases that are initiated or exasperated by air, water, and soil pollution; lack of confidence to adopt the work ethic required for long-term achievements; and global warming that threatens to trigger more severe climate changes by releasing methane and other greenhouse gases from previously frozen soils, melting ice packs, and anaerobic processes in sediments on ocean floors, rivers, lakes, and riparian areas.

SUMMARY

Techniques, systems, apparatus and materials are disclosed for thermochemical repurposing, recycling or reinvestment of carbon dioxide into liquid fuel.

In one aspect, a method of recycling carbon to produce a renewable fuel includes harvesting carbon dioxide emitted from an industrial process. Biomass waste is dissociated under an anaerobic reaction to produce hydrogen. The harvested carbon dioxide is reacted with the biomass waste produced hydrogen under pressure and heat to generate a renewable fuel.

Implementations can optionally include one or more of the following features. The renewable fuel can include at least one of alcohol and ether. The alcohol can include at least one of methanol and ethanol. The ether can include dimethyl ether (DME). The DME can be converted to generate a polymer precursor to a durable good. A catalyst can be added to enhance production of the renewable fuel. The catalyst can include at least one of copper-zinc-oxide, deposited sinter mixture of copper, and copper-zinc oxide. The method can include harvesting waste heat rejected from an engine to provide heat used in the reaction. Heat from a renewable energy source including at least one of wind energy, solar energy, running water and geothermal can be generated. The method can include controlling the heat and pressure to generate a select type of the renewable fuel. Hydrogen can be produced from dissociation of the biomass waste at a remote location and transported in through a pipeline. Dissociating the biomass waste can include thermochemically producing hydrocarbons as a transportable precursor to hydrogen at a remote location; transporting in the hydrocarbons through a pipeline; and separating the hydrocarbons into hydrogen and carbon monoxide. The method can further include cleaning the harvested carbon dioxide; and using the cleaned carbon dioxide as a nutrient for green house crops. The method can include using the cleaned carbon dioxide as a buoyant lifter in photosynthesis for plants comprising algae.

In another aspect, a method of recycling carbon to produce a renewable fuel can include harvesting carbon dioxide emitted from an industrial process. The method can include dissociating biomass waste under an anaerobic process to produce carbon monoxide, one or more carbon donors and hydrogen. Thermochemically shifted carbon monoxide and additional hydrogen can be generated by reacting the harvested carbon dioxide with the biomass waste produced one or more carbon donors; and reacting the biomass produced carbon monoxide and the thermochemically shifted carbon monoxide with the biomass produced hydrogen and the additional hydrogen under pressure and heat to generate a renewable fuel.

Implementations can optionally include one or more of the following features. The one or more carbon donors can include at least one of hydrocarbon and alcohol. The renewable fuel can include at least one of alcohol and ether. The alcohol can include at least one of methanol and ethanol. The ether can include dimethyl ether (DME). The method can include converting the DME to generate a polymer precursor to a durable good. The method can include adding a catalyst to enhance production of the renewable fuel. The catalyst can include at least one of transition metal carbides, borides, and nitrides. The transition metal carbides, borides, and nitrides can include at least one of $Fe_3C$, $CO_3C$, $CO_3Fe_3C_2$, $Mn_3C$, $FeC_3$, $CoC_3$, $CoFeC_6$, $MnFeC_6$, $Mn_5C_2$, $MnFeC_6$, $Fe_3Cr_3C_2$, $Fe_3Co_2BNC_2$, $Fe_3VC_2$, $Fe_4NC_2$, $Fe_3MoC_2$, and $Fe_5BNC$. The method can include harvesting waste heat rejected from an engine to provide the heat used in the reaction. The method can include generating heat from a renewable energy source comprising at least one of wind and solar energy source. The method can include controlling the heat and pressure to generate a select type of the renewable fuel. Hydrogen can be produced from dissociation of the biomass waste at a remote location and transported in through a pipeline. Dissociating the biomass waste can include thermochemically producing the hydrocarbon as a transportable precursor to hydrogen at a remote location; transporting in the hydrocarbons through a pipeline; and separating the hydrocarbons into hydrogen and carbon monoxide. The method can further include cleaning the harvested carbon dioxide; and using the cleaned carbon dioxide as a nutrient for green house crops. The method can further include using the cleaned carbon dioxide as a buoyant lifter in photosynthesis for plants comprising algae.

The described techniques and system can potentially provide one or more of the following advantages. For example, widely available hydrocarbon feedstock substances including selections such as methane from anaerobic digestion of wastes and natural gas is dissociated into carbon and hydrogen. Compared to electrolysis of water, more than four-times as much hydrogen can be produced per BTU equivalent by thermal dissociation of natural gas ($CH_4$+HEAT→Carbon Products+$2H_2$).

Co-produced carbon can be used to manufacture equipment to harness solar, wind, moving water, and geothermal resources along with transportation components that are stronger than steel and lighter than aluminum. Application of such carbon to produce equipment that harnesses renewable resources provides many times more clean energy than burning the carbon one time and incurring environmental pollution and greenhouse gas problems.

Utilization of co-produced hydrogen in combined heat and Power (CHP) engine-generators double energy utilization efficiency compared to central power plants. Also, application of fuel injector or multi-fuel injector technology in engines using hydrogen can actually clean the air that enters such engines.

Another benefit and application of such co-produced hydrogen is to react it with carbon dioxide (from bakeries, breweries, and fossil-fired power plants) to produce liquid fuels that can be stored in tanks that now store gasoline or diesel fuel ($3H_2+CO_2 \rightarrow CH_3OH+H_2O$.) This can enable widespread utilization of hydrogen extracted from methane produced from waste biomass or natural gas by conversion of existing engines in the time of a tune up.

In addition, $CO_2$, which would otherwise be released to the environment can be repurposed and recycled to generate renewable energy by reacting with hydrogen donors or carbon donors from biomass waste dissociation. Thus, rather than waste energy in trying to remove carbon, potentially harmful carbon can be repurposed to generate useful source of energy.

BRIEF DESCRIPTION OF THE DRAWINGS

Like reference symbols and designations in the various drawings indicate like elements.

DETAILED DESCRIPTION

Techniques, apparatus and systems are described for implementing thermochemical regeneration reactions in which carbon dioxide ($CO_2$) is harvested from industrial processes and recycled or repurposed to generate renewable fuel, such as methanol fuel. Rather than waste carbon by taking carbon out of $CO_2$, the described techniques repurpose or recycle $CO_2$ in reactions with biomass waste produced hydrogen to generate renewable fuel.

Figure 1:
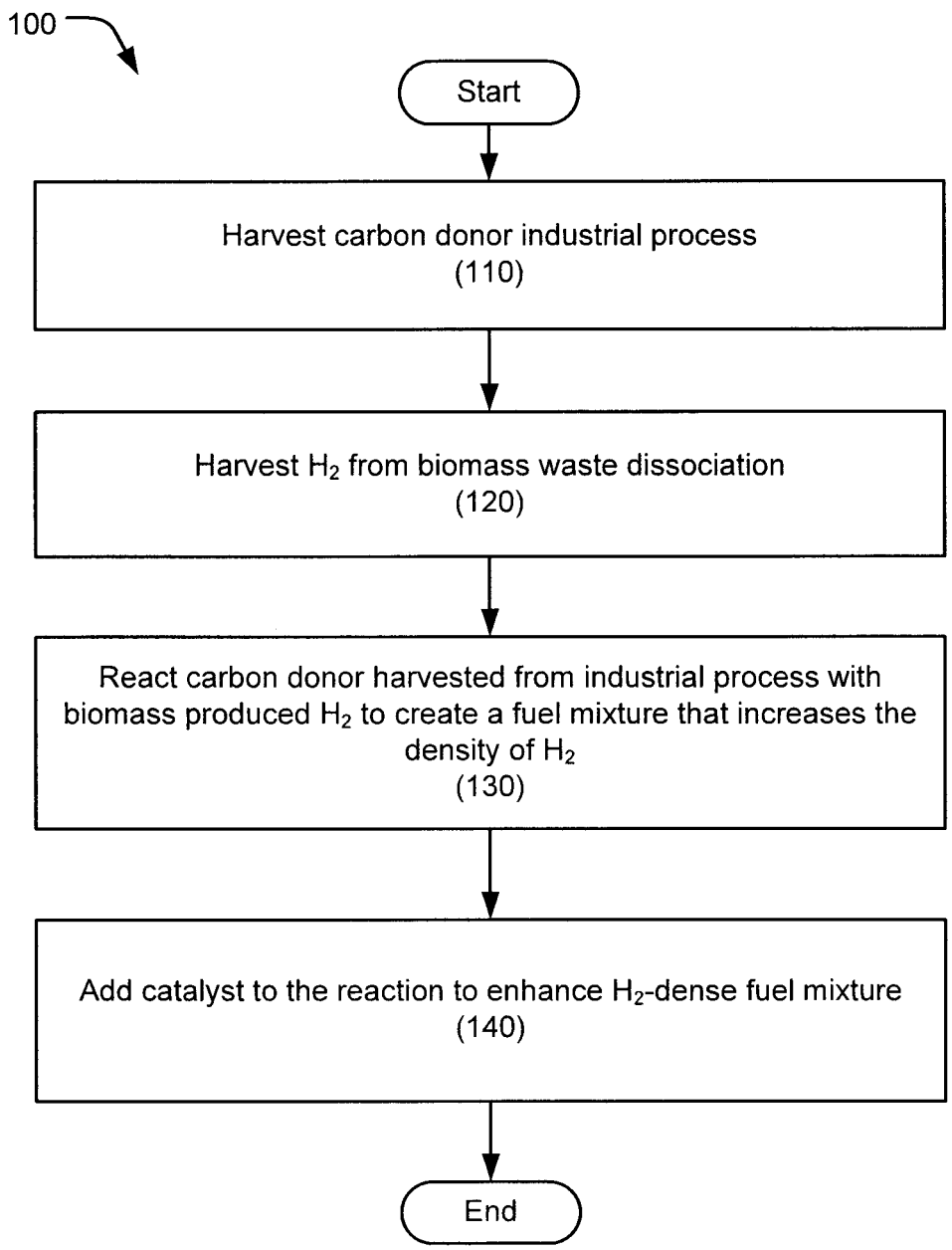
FIG. 1 is a process flow diagram of a process for reinvesting, repurposing or recycling carbon dioxide harvested from waste generated by industrial processes to react with hydrogen from biomass waste dissociation.

FIG. 1 is a process flow diagram of a process 100 for reinvesting, repurposing or recycling carbon dioxide harvested from waste generated by industrial processes to react with hydrogen from biomass waste dissociation. A system (e.g., system 400 below) harvests a carbon donor from industrial processes (110). The carbon donor, such as carbon dioxide or carbon monoxide used in the thermochemical regeneration described here can be harvested from readily available sources of $CO_2$, such as from central power plants, coking, and calcining operations that burn hydrocarbons, breweries, and bakeries. The system obtains hydrogen from biomass waste dissociation (120). The harvested $CO_2$ can be used to produce liquid feedstocks for production of chemicals and or fuels by reacting with the biomass waste produced hydrogen (130). For example, the methanol fuel produced in the described thermochemical regeneration of $CO_2$ with $H_2$ can be used to power gasoline and diesel engines adapted to burn methanol in a non-polluting manner. U.S. Pat. Nos. 6,155,212 and 6,756,140 describe apparatus and techniques for adapting gasoline and diesel engines to burn methanol, the entire contents of which are incorporated by reference.

Equations 1 and 2 below illustrate hydrogen and carbon repurposing or recycling via methanol production in which biomass produced hydrogen is reacted with industrial process produced carbon monoxide (CO) and $CO_2$ respectively.

$$CO+2H_2 \rightarrow CH_3OH (\Delta H = -21.66 \text{ Kcal/g-mol}) \quad \text{Equation 1}$$

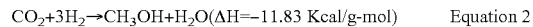

$$CO_2+3H_2 \rightarrow CH_3OH+H_2O (\Delta H = -11.83 \text{ Kcal/g-mol}) \quad \text{Equation 2}$$

The described thermochemical regeneration reactions that recycle or repurpose hydrogen, CO and $CO_2$ provide a bridge technology for increasing the financial return on past investments in equipment by utilizing existing transportation engines and storage tanks to enable thermochemical regeneration reactions (see Equation 5 below) to produce hydrogen-characterized fuels for achieving longer engine life and greater fuel efficiency along with greatly reduced emissions of carbon dioxide, hydrocarbons, oxides of nitrogen and particulates.

The methanol synthesis process summarized in Equations 1 and 2 may be implemented by various steps including catalytic synthesis at 95 to 100 atmospheres pressure and 500° F. (260° C.) (140). Catalysts for the processes of Equations 1 and 2 can include copper-zinc-oxide and deposited sinter mixture of copper and copper-zinc oxide at various process synthesis conditions including about 260° C. (500° F.) and 1500 psi to produce methanol or methanol and water as shown. Alternatively, dimethyl ether (DME) or ethylene or propylene may be produced depending upon the pressure, temperature and catalysts chosen.

Hydrogen used in the above described thermochemical regeneration (Equations 1-2) can be produced from biomass dissociation according to the processes summarized in Equations 3 and 4 below. The details of the biomass waste conversion are described in a copending U.S. patent application Ser. No. 13/027,068 filed Feb. 14, 2011, now U.S. Pat. No. 8,318, 997, and entitled "Carbon-Based Durable Goods and Renewable Fuel from Biomass Waste Dissociation," the entire contents of which are incorporated by reference. Specifically, Equations 3 and 4 summarize a process for dissociating hydrocarbons, such as methane produced by biomass dissociation in an endothermic reaction to generate hydrogen and carbon.

$$C_xH_y + HEAT \rightarrow xC + 0.5yH_2 \qquad \text{Equation 3}$$

$$CH_4 + HEAT \rightarrow C + 2H_2 (\mu H_{298K} = 74.9 \text{ kJ/mol}) \qquad \text{Equation 4}$$

$$C_xH_y + HEAT \rightarrow xC + 0.5yH_2 \qquad \text{Equation 3}$$

$$CH_4 + HEAT \rightarrow C + 2H_2 (\Delta H_{298K} = 74.9 \text{ kJ/mol}) \qquad \text{Equation 4}$$

In addition to co-production by dissociation of hydrocarbon (CxHy) compounds, hydrogen can be derived by electrolytic splitting of water using any clean, alternative energy source. Also, hydrogen can be derived from a non-$CO_2$ producing anaerobic dissociation of organic materials and/or by utilization of energy sources such as wind, hydro, biomass, solar, tidal, geothermal, or off-peak nuclear power plants. Hydrogen can also be produced from virtually any biomass waste that ordinarily rots or burns. Carbon-neutral liquid compounds for storage of hydrogen can be synthesized from hydrogen and carbon dioxide. Also, hydrogen may be produced at or near the site or delivered from pipelines that are transporting hydrogen.

Methanol produce by the thermochemical regeneration reactions as described above (see Equations 1 and 2) can be inexpensive, storable and transportable. In one implementation of the carbon-neutral hydrogen storage operation, methanol is synthesized from sources that ordinarily source emissions of $CO_2$. Such $CO_2$ can be captured from ethanol plants, bakeries, breweries, Portland cement plants, and fossil burning power plants and/or by atmospheric "scrubbing" to extract up to about three molecules of carbon dioxide from ten thousand molecules of air.

Similar to ethanol, methanol can be blended with gasoline up to 20% in conventional engines and 85% in flex fuel vehicles with no modifications to the vehicle or existing transportation fuel infrastructure. For years, methanol, with an octane rating of 100, has been used as a racing fuel for high-performance cars and dragsters.

Primary use of alcohols such as methanol as an energy carrier is economically and energetically favorable. For example, one liter of methanol at ambient temperature contains more hydrogen than one liter of liquid hydrogen that must be maintained in storage at −421° F.

Figure 2:
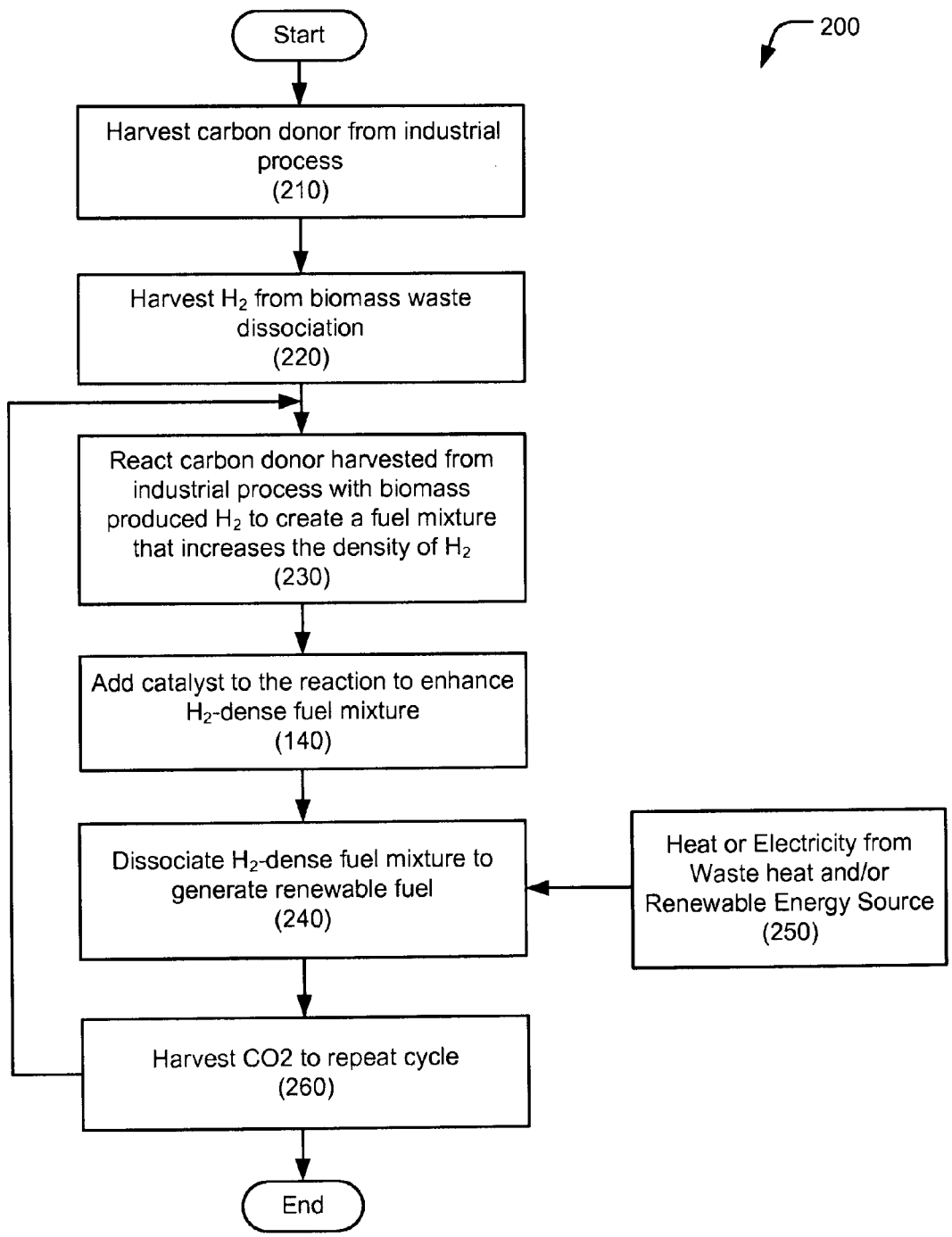
FIG. 2 is a process flow diagram of an exemplary process for generating oxidized fuel and hydrogen fuel by dissociating the $H_2$-dense fuel mixture generated by reacting repurposed or recycled $CO_2$ from industrial waste with hydrogen from biomass waste.

FIG. 2 is a process flow diagram of an exemplary process 200 for generating oxidized fuel and hydrogen fuel by dissociating the $H_2$-dense fuel mixture generated by reacting repurposed or recycled $CO_2$ from industrial waste with hydrogen from biomass waste. A system (e.g., system 300 below) harvests a carbon donor from industrial processes (210). The carbon donor, such as carbon dioxide or carbon monoxide used in the thermochemical regeneration described here can be harvested from readily available sources of $CO_2$, such as from central power plants, coking, and calcining operations that burn hydrocarbons, breweries, and bakeries. The system obtains hydrogen from biomass waste dissociation (220). The harvested $CO_2$ can be used to produce liquid feedstocks for production of chemicals and or fuels by reacting with the biomass waste produced hydrogen (230). For example, the methanol fuel produced in the described thermochemical regeneration of $CO_2$ with $H_2$ can be used to power gasoline and diesel engines adapted to burn methanol in a non-polluting manner. U.S. Pat. Nos. 6,155,212 and 6,756,140 describe apparatus and techniques for adapting gasoline and diesel engines to burn methanol, the entire contents of which are incorporated by reference. The methanol synthesis process summarized in Equations 1 and 2 may be implemented by various steps including catalytic synthesis at 95 to 100 atmospheres pressure and 500° F. (260° C.) (140). As described above, catalysts for the processes of Equations 1 and 2 can include copper-zinc-oxide and deposited sinter mixture of copper and copper-zinc oxide at various process synthesis conditions including about 260° C. (500° F.) and 1500 psi to produce methanol or methanol and water as shown.

As shown in Equation 5, methanol can be thermochemically reformed or dissociated in a second reaction with waste heat (e.g., reinvested or recycled from a solar dish or engine exhaust) and/or water to produce oxides of carbon and hydrogen fuel (240).

$$CH_3OH + H_2O + heat \rightarrow CO + 3H_2 \qquad \text{Equation 5}$$

Power and heat supplied by an engine, solar concentrator, or other ordinarily wasted or renewable sources can supply the energy or heat needed for the endothermic operations and processes for generating the renewable fuel, such as the $H_2$-dense fuel (250). By incorporating energy recovered from ordinarily wasted heat, the new fuel species produced by thermochemical regeneration can release 15 to 25% more energy upon combustion than the original alcohol feed stocks.

Similarly to Equation 5, low-cost fuel and water mixtures, such as hydrocarbons and water with an emulsifier or an alcohol, such as methanol and water as shown in Equation 2 may be thermochemically reformed into new fuel species such as carbon dioxide and hydrogen for separation or direct use as a mixture for injection into the combustion chamber of an engine as shown in Equation 6.

$$CH_3OH + H_2O \rightarrow CO_2 + 3H_2 \qquad \text{Equation 6}$$

This yields a much more powerful fuel—primarily hydrogen. This fuel can be burned in an engine (to generate electricity and/or for transportation) and produce clean water as a byproduct as shown in Equation 7.

$$CO + 3H_2 + 2O_2 \rightarrow 3H_2O + CO_2 \qquad \text{Equation 7}$$

The $CO_2$ byproduct can be harvested and repurposed or recycled in a reaction with hydrogen produced from biomass dissociation to continuously repeat the cycle (260).

Whereas hydrogen used in fuel-cell technology should be pure (and therefore is expensive to produce), hydrogen used in internal combustion engines can be impure. The described process of thermochemical regeneration is just as effective with impure or dirty hydrogen as it is with expensive, pure hydrogen. For example, hydrogen made from black water, organic wastes, or sewage has organic carbon as an impurity. However, just as the $CO_2$ is being prevented from becoming an atmospheric pollutant, hydrogen sourced from bio-wastes provides an additional benefit of reducing pollution from this inexpensive and sustainable resource. In each instance, energy, which would otherwise be lost as waste can be harvested and repurposed or recycled to generate renewable fuel.

Catalysts that improves the rate of the processes of Equations 6-7 can include transition metal carbides, borides, and nitrides including non-stoichiometric mixtures and/or intermetallic compounds with approximate formulas such as $Fe_3C$, $Co_3C$, $Co_3Fe_3C_2$, $Mn_3C$, $FeC_3$, $CoC_3$, $CoFeC_6$, $MnFeC_6$, $Mn_5C_2$, $MnFeC_6$, $Fe_3Cr_3C_2$, $Fe_3Co_2BNC_2$, $Fe_3VC_2$, $Fe_4NC_2$, $Fe3MoC_2$, and $Fe_5BNC$.

It may be desired to operate such processes cyclically with electrolysis being performed at times that electricity is inexpensive or when surplus electricity is available from intermittent magnitudes of renewable energy production. Thus a fluid product that has less density than the feedstock can be restricted from expansion until the pressure desired is achieved for storage, transmission by a fluid conduit, to generate heat by combustion or catalytic oxidation or for a chemical process such as a fuel cell or a regenerative electrolyzer/fuel cell or physical reaction including reactions that are aided by pressurization.

As an example, marine applications such as large cargo ship engines can be made to utilize a cheap petrochemical like paraffin with the resulting propulsion process producing clean water and hydrogen in storage by the end of the trip. By utilizing the power for transportation, the waste heat byproduct from the engines is used to drive the continuing thermo chemical regeneration—improves overall efficiency and transforms wastes and pollutive products into energy carriers and productive energy. A vessel utilizing such technologies could be propelled while hydrogen or methanol is produced for fueling aircraft, missiles, unmanned reconnaissance probes, and new tactical weapons.

In another aspect, the techniques, apparatus and systems described herein readily accepts solutions of water and fuels including oxygenated constituents. The ability to utilize solutions of water and fuels provides various advantages including: 1) saving energy needed to dry or remove water from oxygenated fuel constituents; 2) reducing fuel production cost by avoiding the equipment and energy expenses required to produce and store water-free fuels; 3) reducing toxicity by reducing or eliminating the concentration gradient between water solutions within living cells and the fuel-water solution; 4) and to facilitate beneficial thermochemical regeneration production of more energetic and faster burning hydrogen-characterized fuels (see Equations 8, 9, and or 10 below).

Figure 3A:
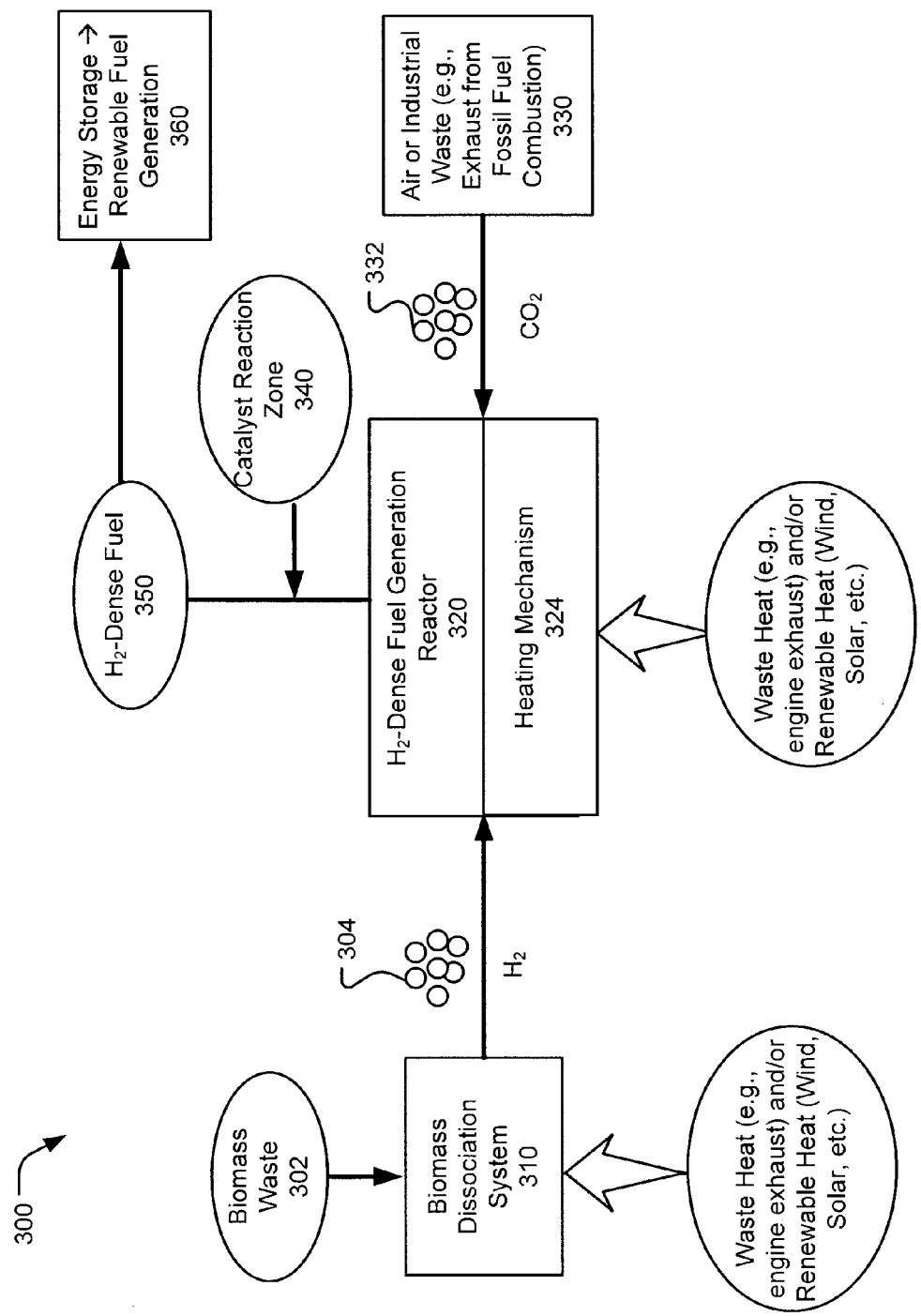
FIG. 3A is a block diagram showing an exemplary system for repurposing or recycling $CO_2$ harvested from industrial processes as waste to create renewable fuel by reacting with biomass produced hydrogen.

FIG. 3A is a block diagram showing an exemplary system 300 for repurposing or recycling $CO_2$ harvested from industrial processes as waste to create renewable fuel by reacting with biomass produced hydrogen. The system 300 includes a biomass dissociation system 310 that receives biomass waste 302 to be dissociated into carbon, hydrocarbons, alcohols, ammonia and hydrogen using a thermochemical regenerative process. The heat used to dissociate the biomass waste 302 can include waste heat from engine exhausts, engine cooling system etc. that otherwise would be released to the environment. Also, one or more of renewable energy sources, such as wind, solar, etc. can be used to generate the heat.

From the biomass dissociation system 310, low specific energy hydrogen 304 (from dissociation of hydrocarbons, for example) is captured and forwarded to $H_2$-dense fuel generating reactor 320, which includes a heating mechanism 324. The $H_2$-dense fuel generating reactor 320 also receives carbon donors, such as $CO_2$ 332 harvested from industrial processes (e.g., exhaust gases from fossil fuel combustion or air). The $H_2$-dense fuel generating reactor 320 causes the low specific energy $H_2$ to react with the harvested carbon donors, such as $CO_2$ 332 to generate $H_2$-dense fuel 350, such as methanol. The carbon donors 332 can be obtained from air or industrial waste 330 (e.g., exhaust from fossil fuel combustion).

The system 300 can include a catalyst reaction zone 340 to receive one or more catalysts that enhances the generation of the $H_2$-dense fuel mixture. Examples of catalysts are described above.

The generated $H_2$-dense fuel mixture 350 is storable and transportable. Because the $H_2$-dense fuel mixture 350 carry $H_2$ fuel in a transportable form, the $H_2$-dense fuel mixture operates as a vehicle for carry energy to a desired destination. The $H_2$-dense fuel 350 mixture can be dissociated to obtain $H_2$ fuel and oxygenated fuel using a renewable fuel generation system 360.

Figure 3B:
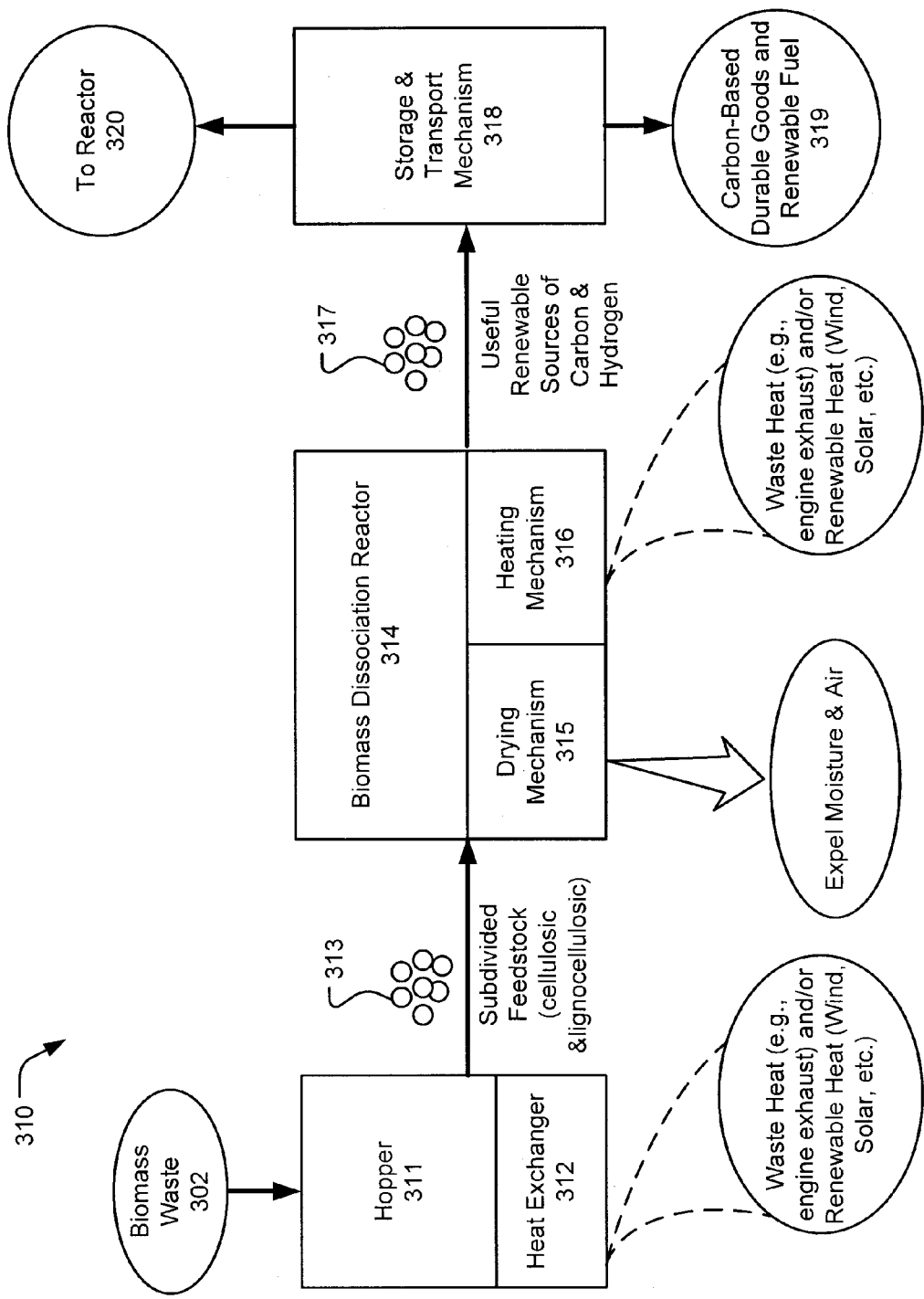
FIG. 3B is a block diagram showing an exemplary system for dissociating biomass waste into hydrogen and carbon carrying intermediaries.

FIG. 3B is a block diagram showing an exemplary system 310 for dissociating biomass waste into hydrogen and carbon carrying intermediaries. The system 310 includes a biomass waste intake component, such as a hopper 311 that receives the biomass waste 302 in raw form and breaks down (e.g., chips, chops, grinds, etc.) the raw material into subdivided feedstock, such as various cellulosic and lignocellulosic materials. The hopper 311 can include a heating mechanism, such as a heat exchanger 312 to pre-heat the subdivided feedstock. The heat exchanger can recapture and recycle waste heat from an external heat source (e.g., engine exhaust and/or renewable heat, such as wind, solar, etc.) or from biomass dissociation reactor 314 itself.

The subdivided (and in some implementations, pre-heated) feedstock 313 is forwarded to a biomass dissociation reactor 314 to dissociate the biomass waste feedstock into useful renewable sources of carbon and hydrogen, such as various hydrocarbons, alcohols, ammonia, and oxides of carbon. The reactor can include a drying mechanism 315 to expel moisture and air from the feedstock. The drying mechanism 315 can include an extruding device to physically 'squeeze out' the moisture and air from the feedstock. Examples of the extruding device include a helical screw conveyer and a ram piston conveyer. Also, the drying mechanism 315 can include one or more heating mechanisms, such as heat exchangers that capture heat generated by the reactor 314 and recycle the captured heat to dry the feedstock. The heat exchangers can also recapture and recycle waste heat from an external heat source (e.g., engine exhaust and/or renewable heat, such as wind, solar, etc.)

The reactor 314 can also include a heating mechanism 316 for generating adequate heat used in an anaerobic reaction to dissociate the biomass waste feedstock into the useful renewable sources of carbon and hydrogen 317, such as hydrocarbons, alcohols, ammonia and oxides of carbon. The generated useful renewable sources of carbon and hydrogen 317 can be forwarded to a storage and/or transport mechanism 318 to be used by the H2-dense fuel generation reactor 320 and in additional reactions to generate renewable fuel and/or carbon-based durable goods 319 as described in the copending U.S. patent application entitled "Carbon-Based Durable Goods and Renewable Fuel from Biomass Waste Dissociation," the entire contents of which is incorporated by reference. Moreover, the storage and/or transport mechanism 318 allows for efficient transport of the useful renewable sources of carbon and hydrogen 317 to remote locations for further processing.

The biomass dissociation reactor 314 can be configured to increase the thermal efficiency of the biomass waste conversion process while reducing or eliminating carbon dioxide formation. For example, the biomass dissociation reactor 314 can include mechanisms to perform various countercurrent drying (e.g., recycling heat) and elimination of air, moisture, and other oxygen donors prior to extraction of carbon, hydrocarbons such as methane, and/or hydrogen.

Figure 3C:
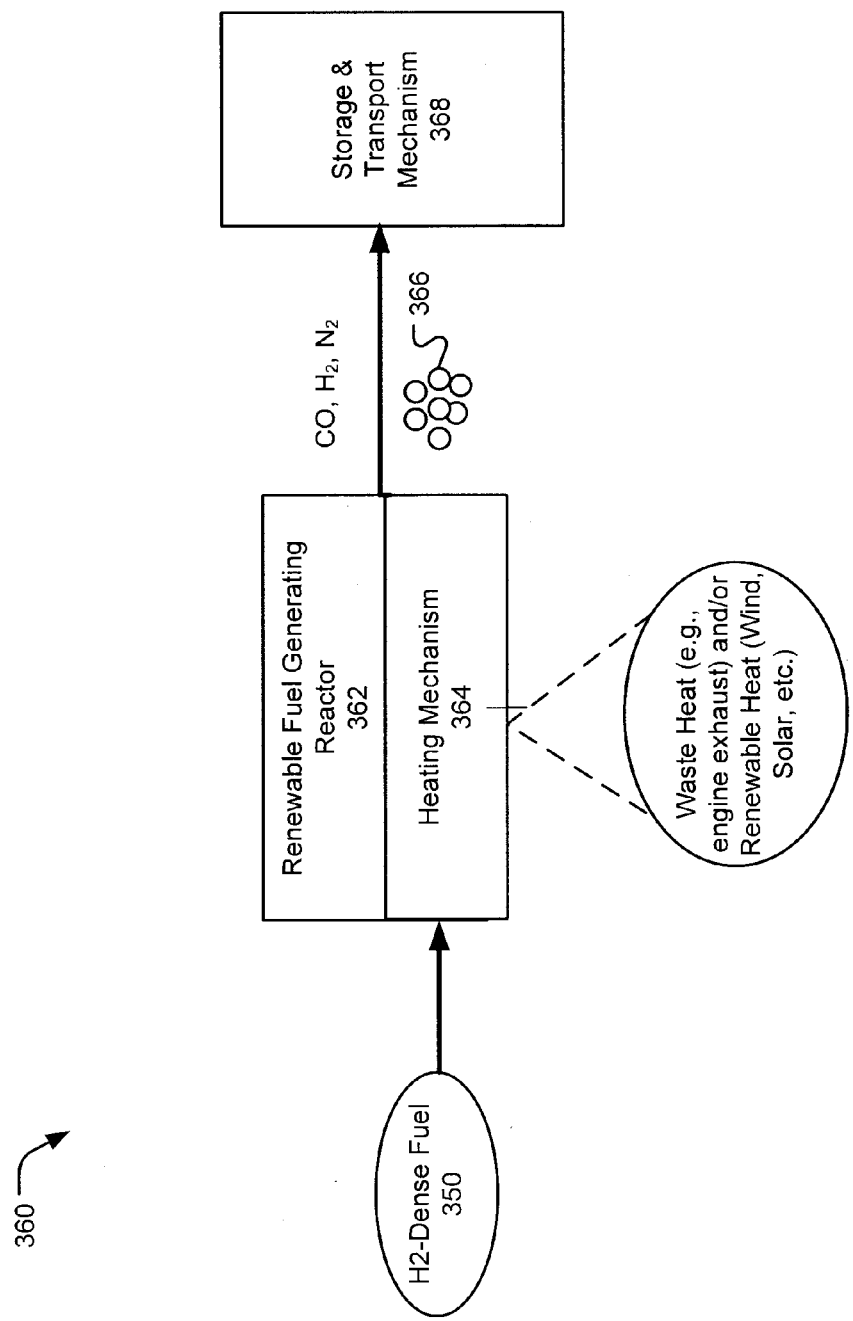
FIG. 3C is a block diagram showing an exemplary system for generating multi-purpose $H_2$-dense fuel for isolating hazardous contaminants and for storing energy as described above.

FIG. 3C is a block diagram showing an exemplary system 360 for generating multi-purpose $H_2$-dense fuel for isolating hazardous contaminants and for storing energy as described above. The system 360 includes a renewable fuel generating reactor 362 that receives the $H_2$-dense fuel 350 generated as described above. The renewable fuel generating reactor 362 can include a heating mechanism 364 to apply heat necessary to covert the $H_2$-dense fuel mixture into renewable fuel and nutrients 366, such as oxides of carbon, hydrogen, and nitrogen. The heat used in the reaction can be obtained from waste heat from engine exhaust or cooling system that otherwise would be released to the environment. Also, heat from one or more renewable resources, such as wind, solar, running water, geothermal, etc. can be used in the reaction. In addition, the generated renewable fuel can be stored and/or transported to other location using storage and transport mechanism 368, such as a pressurized container or pipelines.

Figure 4:
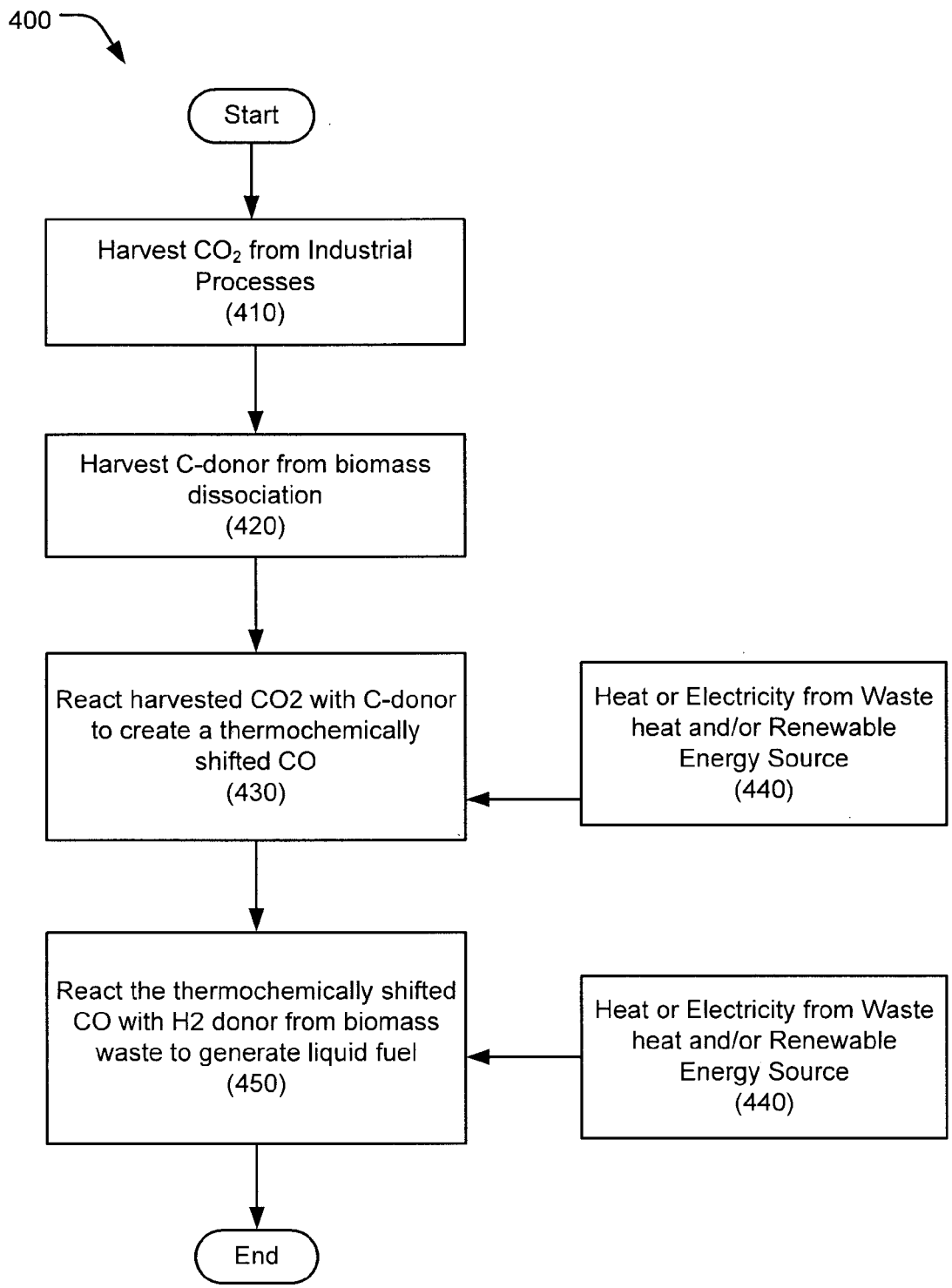
FIG. 4 shows a process flow diagram for a process for using harvested $CO_2$ (e.g., from fossil fuel combustion waste) as a source of thermochemically shifted CO by reacting the fossil produced carbon dioxide with a renewable carbon donor.

FIG. 4 shows a process flow diagram for a process 400 for using harvested $CO_2$ (e.g., from fossil fuel combustion waste) as a source of thermochemically shifted CO by reacting the fossil produced carbon dioxide with a renewable carbon donor. A system (e.g., system 500 below) can collect $CO_2$ from industrial processes including bakeries, breweries, calcining plants, and other sources such as power plants, fuel cells and engines that use carbonaceous fuels (410). Carbon monoxide may also be provided by the process summarized in Equation 8 for methanol producing processes such as those generally depicted by Equation 1 above. The system can obtain a carbon donor produced by the hydrocarbon (produced from biomass waste) dissociation processes summarized in Equations 3 and 4 above (420). The carbon donor from hydrocarbon dissociation can be reacted with the harvested $CO_2$ in presence of adequate heat to produced thermochemically shifted CO (430) as shown in Equation 8 below.

$$CO_2 + C + ENERGY \rightarrow 2CO \qquad \text{Equation 8}$$

The carbon donor for this purpose may also be delivered and donated by utilizing condensable liquid fuel constituents such as methanol to be reacted with harvested $CO_2$. It can be advantageous to utilize a renewable energy resource (e.g., methane from biomass) to provide carbon for processing carbon dioxide into carbon monoxide as shown in Equation 9.

$$CH_4 + CO_2 + ENERGY \rightarrow 2CO + 2H_2 \qquad \text{Equation 9}$$

The heat used in the reaction of the harvested $CO_2$ with the biomass waste generated carbon donor can include waste heat from engine exhausts, engine cooling system etc. that otherwise would be released to the environment (440). Also, one or more of renewable energy sources, such as wind, solar, etc. can be used to generate the heat.

Higher pressure hydrogen can be used to pressurize the products of Equation 9, such as carbon monoxide and hydrogen. Also, the higher pressure hydrogen can be produced by other energy induced dissociations including electrolysis of anaerobically developed acids and liquors from organic digestion processes and from water as generally shown in Equations 3, 4, 10 and 11.

$$C_2H_4O_2 + 2H_2O + ENERGY \rightarrow 2CO_2 + 4H_2 \qquad \text{Equation 10}$$

$$H_2O + ENERGY \rightarrow 0.5O_2 + H_2 \qquad \text{Equation 11}$$

Pressurized hydrogen or pressurized and heated hydrogen such as may be produced by the pressurizing processes shown in Equations 3, 4, 10, and or 11 can be added to pressurize the products of Equation 9 to form a desired compound such as DME fuel or methanol as shown in Equation 12 (450).

$$CO + H_2 + H_2 \rightarrow CH_3OH \qquad \text{Equation 12}$$

Liquid fuel such as methanol provided by the processes summarized in Equations 1 and 12 can readily be stored, transported, metered and dispensed by equipment and systems typically utilized for diesel, gasoline, and other alcohol fuels.

Equation 13 shows the process steps of dissociating carbon monoxide such as carbon monoxide from processes summarized in Equation 5 or from other sources to provide partial oxidation of methane to produce methanol and or DME.

$$CH_4 + CO + ENERGY \rightarrow CH_3OH + C \qquad \text{Equation 13}$$

The process summarized in Equation 13 may be performed on or in the presence of activated carbon and the carbon produced as oxygen is utilized to form methanol may be precipitated to add to the inventory of such carbon. Facilitation of the reaction may be provided by a reactor that utilizes activated carbon to adsorb carbon monoxide that is dissociated with or without the aid of catalysts to release oxygen that partially oxidizes methane to form methanol.

The heat used in the reaction of the harvested $CO_2$ with the biomass waste generated carbon donor can include waste heat from engine exhausts, engine cooling system etc. that otherwise would be released to the environment (440). Also, one or more of renewable energy sources, such as wind, solar, etc. can be used to generate the heat.

Repurposing or recycling of oxides of carbon such as carbon dioxide or carbon monoxide from air-burning processes generally poses the problem of separation or accommodation of nitrogen contamination. Another process variation for preparation of values from mixtures of reactive ionic species is provided by arc, corona, microwave, or radiative ionization. Mixtures carbon monoxide including production by the process of Equation 5, and hydrogen including production by the process of Equations 3 or 4, and such nitrogen are reacted to produce $CH_3OH$ and $NH_3$ as shown in Equation 14.

$$CO + 5H_2 + N_2 + ENERGY \rightarrow CH_3OH + 2NH_3 \qquad \text{Equation 14}$$

Ammonia ($NH_3$) produced by this or other reactions that utilize hydrogen produced by the processes typical to Equations 3 or 4, can be safely stored and conveyed. This provides compact storage and may serve as a precursor of hydrogen. Ammonia can be stored in various ways including as a pressurized liquid, a salt such as ammonium chloride, or in activated media such as carbon and pressurization can be accomplished by heat addition. Decomposition of ammonia as it passes a catalyst may be utilized to pressurize the $N_2$ and $H_2$ products including pressurization of carbon monoxide and hydrogen that may be co-produced from methanol or wet methanol.

Figure 5:
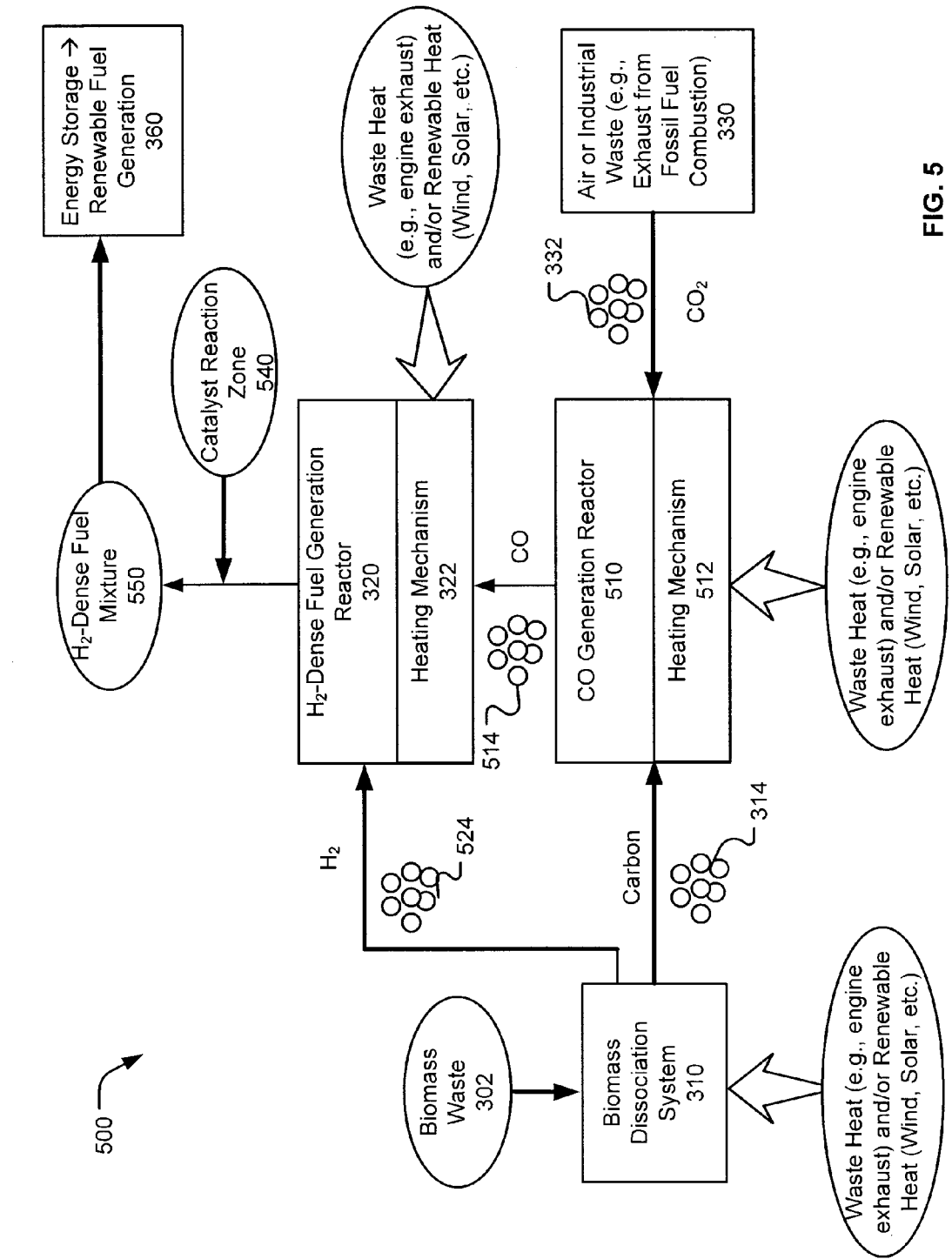
FIG. 5 is a block diagram of an exemplary system for generating renewable fuel from thermochemically shifted CO reacted with hydrogen from biomass waste dissociation.

FIG. 5 is a block diagram of an exemplary system 500 for generating renewable fuel from thermochemically shifted CO reacted with hydrogen from biomass waste dissociation. The system 500 includes a biomass dissociation system 310 that receives biomass waste 302 to be dissociated into carbon, hydrocarbons, alcohols, ammonia and hydrogen using a thermochemical regenerative process. The heat used to dissociate the biomass waste 302 can include waste heat from engine exhausts, engine cooling system etc. that otherwise would be released to the environment. Also, one or more of renewable energy sources, such as wind, solar, etc. can be used to generate the heat.

From the biomass dissociation system 310, carbon donor 314 (from dissociation of hydrocarbons, for example) is captured and forwarded to a CO generating reactor 510, which includes a heating mechanism 514. The carbon donor 314 is reacted with $CO_2$ harvested from industrial processes (e.g., exhaust gases from fossil fuel combustion or air). The CO generating reactor 510 can cause the carbon donor to react with the harvested $CO_2$ 332 obtained from air or industrial processes (e.g., exhaust from fossil fuel combustion, waste stream of a polymer plant, etc.) to generate CO 514.

The thermochemically shifted CO 514 is forwarded to a $H_2$-dense fuel generating reactor 320, which includes a heating mechanism 324. The $H_2$-dense fuel generator 320 also receives hydrogen donors 524 harvested from biomass waste dissociation system 310. The $H_2$-dense fuel generating reactor 320 can cause the hydrogen donors 524 (e.g., low specific energy $H_2$) to react with the shifted CO 514 to generate $H_2$-dense fuel 550, such as methanol. The heat used to generate the $H_2$-dense fuel mixture 550 can include waste heat from engine exhausts, engine cooling system etc. that otherwise would be released to the environment. Also, one or more of renewable energy sources, such as wind, solar, running water, geothermal, etc. can be used to generate the heat.

The system 500 can include a catalyst reaction zone 540 to receive one or more catalysts that enhances the generation of the $H_2$-dense fuel mixture. Examples of catalysts are described above.

The generated $H_2$-dense fuel mixture 550 is storable and transportable. Because the $H_2$-dense fuel mixture 550 carry $H_2$ fuel in a transportable form, the $H_2$-dense fuel mixture operates as a vehicle for carry energy to a desired destination. The $H_2$-dense fuel 550 mixture can be dissociated to obtain $H_2$ fuel and oxygenated fuel using a renewable fuel generation system 360.

Figure 6:
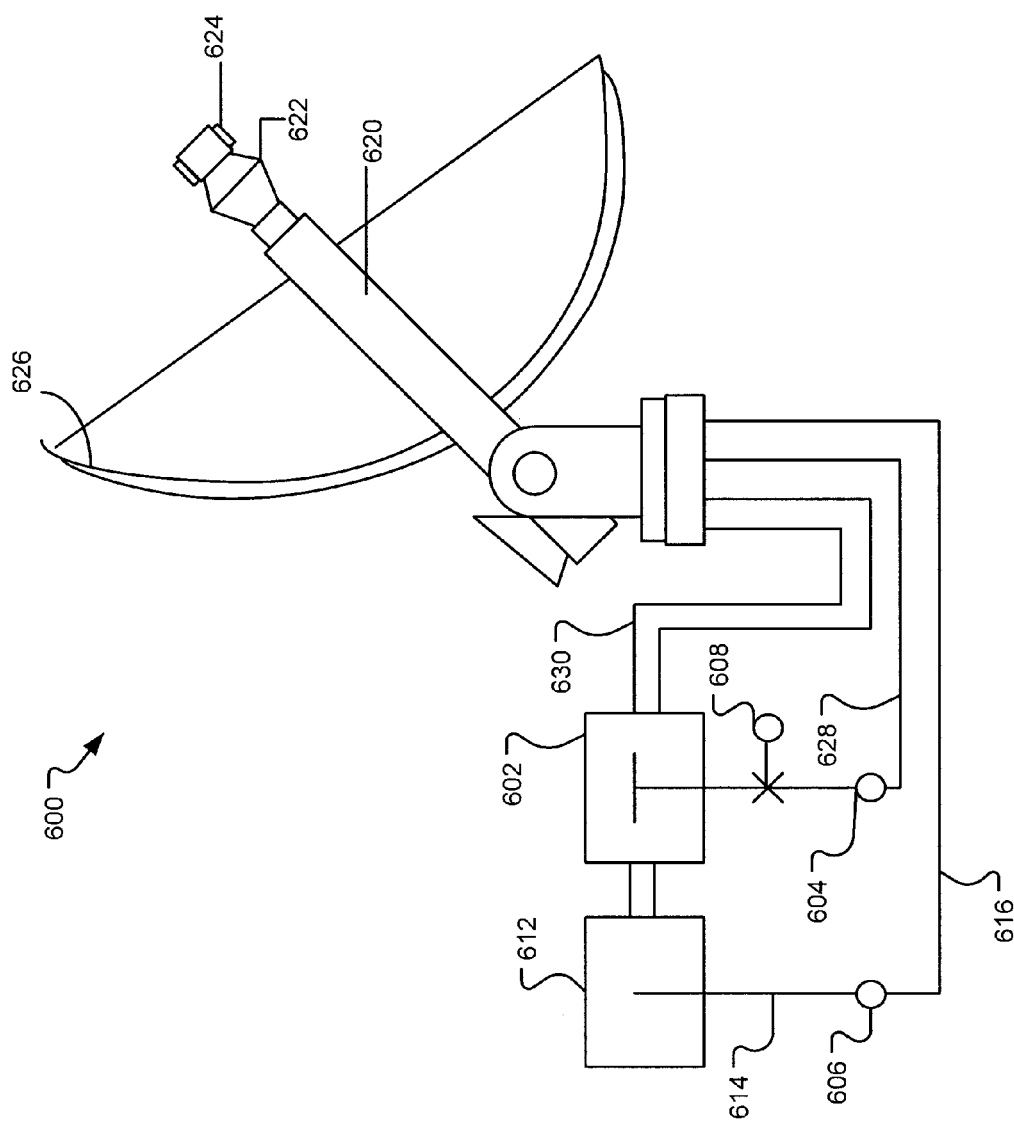
FIG. 6 is a block diagram of an exemplary system for repurposing or recycling carbon and hydrogen.

FIG. 6 is a block diagram of an exemplary system 600 for repurposing or recycling carbon and hydrogen. Hydrogen generated from hydrocarbon dissociation as in Equation 1 can be used in an engine 602 such as a gas turbine or positive displacement engine such as a rotary combustion or piston engine and the output of the engine can be applied to a load such as a pump or generator 612 as shown. The exhaust from the engine 602 may be used as a heat supply for the endothermic reactions previously disclosed and or it may be delivered through conduit 630 to a heat exchanger 620 for receiving heat from a suitable source such as solar concentrator 626 which may be of any suitable design including a trough, dish, or a Fresnel lens. Hydrogen may be supplied by pipeline 604 including arrangements for subterranean delivery of relatively pure hydrogen from an industrial park that produces durable goods from carbon as shown in Equation 1 or hydrogen may be interchangeably delivered in a mixture with other fuels such as natural gas.

The exhaust from the engine 602 may source heat for various other purposes including the previously described endothermic processes and a portion of the exhaust may be further heated by the solar concentrator 626 to provide high temperature gas for expansion in an engine such as a turbine 622 and the output of such work production may be applied to a pump or generator 624. Electricity produced by generator 624 may be delivered through a cable 616 for distribution by a collector cable 606 as electricity delivered to 606 through 614 from generator 612. Fuel from pipe 604 may be delivered by line 628 and controlled by a pump or valve 608 for combustion in engine 622 for operation at times insufficient solar energy is available to enable the system to meet demands for electricity.

Depending upon demand for power and available solar energy, additional working fluid such as air or water may be delivered to a conduit 630 to provide peaking power by maximizing the output of the dish 626 and the engine 622.

Tangible and Useful Applications

The Ethanol Industry has developed an excellent market opportunity for methanol production. Ethanol plants emit millions of tons each year of $CO_2$ through the fermentation process. This $CO_2$ can be readily collected and combined with hydrogen to produce methanol. A 50 million gallon per year ethanol plant would produce an additional 30 million gallons of methanol from the waste $CO_2$ emissions. This would improve the productivity of the ethanol plant by 60%.

One of the key factors to producing methanol from this process at a competitive price is low-cost electricity. Since most ethanol plants either have favorable contracts or produce low-cost electricity, these plants have access to low-cost electricity. Also, the ethanol plants already have the transportation and marketing infrastructure in place to handle the increased volume in liquid transportation fuels.

In some implementations, methanol can be used to "denature" ethanol, replacing costly gasoline.

Applying the described techniques to new ethanol plants currently under construction can potentially provide an additional 3.3 billion gallons of environmentally friendly alternative fuels annually through the waste $CO_2$ emissions from the fermentation process of the ethanol plants. This number could easily be doubled if applied to the existing ethanol plants.

In some implementations, the contaminated or 'dirty' carbon dioxide harvested from various industrial processes as described above can be cleaned and used as nutrients (e.g., along with water) for greenhouse crops. In addition, the clean carbon dioxide can be used as a buoyant lifter or pump in photosynthesis for plants, such as algae. Thus, the cleaned carbon dioxide can be recycled and repurposed as plant nutrients or a pump in photosynthetic reactions.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application. For example, the described techniques, systems and apparatus can be implemented to provide carbon extraction from any hydrogen and carbon containing material. The extracted carbon can be used to manufacture equipment to harness solar, wind, moving water, and geothermal resources along with transportation components that are stronger than steel and lighter than aluminum. Also, application of such extracted carbon to produce these equipments can provide many times more clean energy than burning the carbon one time and incurring resulting environmental pollution and greenhouse gas problems.

To the extent not previously incorporated herein by reference, the present application incorporates by reference in their entirety the subject matter of each of the following materials: U.S. patent application Ser. No. 12/857,553, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,541, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010, now U.S. Pat. No. 8,808,529, and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010 and titled ENERGY SYSTEM FOR DWELLING SUPPORT; U.S. patent application Ser. No. 13/027,235, filed on Feb. 14, 2011, now U.S. Pat. No. 8,313,556, and titled DELIVERY SYSTEMS WITH IN-LINE SELECTIVE EXTRACTION DEVICES AND ASSOCIATED METHODS OF OPERATION; U.S. Provisional Patent Application No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. patent application Ser. No. 13/027,208, filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; U.S. patent application Ser. No. 13/026,996, filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; U.S. patent application Ser. No. 13/027,015, filed on Feb. 14, 2011 and titled CHEMICAL REACTORS WITH RE-RADIATING SURFACES AND ASSOCIATED SYSTEMS AND METHODS; U.S. patent application Ser. No. 13/027,244, filed on Feb. 14, 2011 and titled THERMAL TRANSFER DEVICE AND ASSOCIATED SYSTEMS AND METHODS; U.S. patent application Ser. No. 13/026,990, filed on Feb. 14, 2011, now U.S. Pat. No. 8,187,549, and titled CHEMICAL REACTORS WITH ANNULARLY POSITIONED DELIVERY AND REMOVAL DEVICES, AND ASSOCIATED SYSTEMS AND METHODS; U.S. patent application Ser. No. 13/027,181, filed on Feb. 14, 2011, now U.S. Pat. No. 8,187,550, and titled REACTORS FOR CONDUCTING THERMOCHEMICAL PROCESSES WITH SOLAR HEAT INPUT, AND ASSOCIATED SYSTEMS AND METHODS; U.S. patent application Ser. No. 13/027,215, filed on Feb. 14, 2011, now U.S. Pat. No. 8,318,269, and titled INDUCTION FOR THERMOCHEMICAL PROCESS, AND ASSOCIATED SYSTEMS AND METHODS; U.S. patent application Ser. No. 13/027,198, filed on Feb. 14, 2011 and titled COUPLED THERMOCHEMICAL REACTORS AND ENGINES, AND ASSOCIATED SYSTEMS AND METHODS; U.S. Provisional Patent Application No. 61/385,508, filed on Sep. 22, 2010 and titled REDUCING AND HARVESTING DRAG ENERGY ON MOBILE ENGINES USING THERMAL CHEMICAL REGENERATION; U.S. patent application Ser. No. 13/027,060, filed on Feb. 14, 2011, now U.S. Pat. No. 8,318,100, and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; U.S. Provisional Patent Application No. 61/237,419, filed on Aug. 27, 2009 and titled CARBON SEQUESTRATION; U.S. patent application Ser. No. 13/027,068, filed on Feb. 14, 2011, now U.S. Pat. No. 8,318,997, and titled CARBON-BASED DURABLE GOODS AND RENEWABLE FUEL FROM BIOMASS WASTE DISSOCIATION; U.S. patent application Ser. No. 13/027,195, filed on Feb. 14, 2011, now U.S. Pat. No. 8,784,095, and titled OXYGENATED FUEL; U.S. Provisional Patent Application No. 61/237,425, filed on Aug. 27, 2009 and titled OXYGENATED FUEL PRODUCTION; U.S. patent application Ser. No. 13/027,197, filed on Feb. 14, 2011, now U.S. Pat. No. 8,070,835, and titled MULTI-PURPOSE RENEWABLE FUEL FOR ISOLATING CONTAMINANTS AND STORING ENERGY; U.S. Provisional Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; and U.S. patent application Ser. No. 13/027,185, filed on Feb. 14, 2011, now U.S. Pat. No. 8,328,888, and titled ENGINEERED FUEL STORAGE, RESPECIATION AND TRANSPORT.

What is claimed is:

1. A method of recycling carbon to produce a renewable fuel, the method comprising:
   harvesting carbon dioxide emitted from an industrial process;
   dissociating biomass waste under an anaerobic process to produce one or more carbon donors and hydrogen, wherein the biomass produced hydrogen includes low specific energy hydrogen;
   separating the biomass produced hydrogen from the biomass produced one or more carbon donors;
   generating thermochemically shifted carbon monoxide and additional hydrogen by reacting the harvested carbon dioxide with the biomass waste produced one or more carbon donors; and
   reacting the thermochemically shifted carbon monoxide with the biomass produced hydrogen and the additional hydrogen in a hydrogen-dense fuel generating reactor under pressure and heat to cause the low specific energy hydrogen to react with the thermochemically shifted carbon monoxide to generate a hydrogen-dense renewable fuel.

2. The method of claim 1, wherein the one or more carbon donors comprises at least one of hydrocarbon and alcohol.

3. The method of claim 1, wherein the renewable fuel comprises at least one of alcohol and ether.

4. The method of claim 3, wherein the alcohol comprises at least one of methanol and ethanol; and
   the ether comprises dimethyl ether (DME).

5. The method of claim 4, comprising converting the DME to generate a polymer precursor to a durable good.

6. The method of claim 1, comprising adding a catalyst to enhance production of the renewable fuel wherein the catalyst comprises at least one of transition metal carbides, borides, and nitrides.

7. The method of claim 6, wherein the transition metal carbides, borides, and nitrides comprise at least one of $Fe_3C$, $Co_3C$, $Co_3Fe_3C_2$, $Mn_3C$, $FeC_3$, $CoC_3$, $CoFeC_6$, $MnFeC_6$, $Mn_5C_2$, $MnFeC_6$, $Fe_3Cr_3C_2$, $Fe_3Co_2BNC_2$, $Fe_3VC_2$, $Fe_4NC_2$, $Fe3MoC_2$, and $Fe_5BNC$.

8. A method of recycling carbon to produce a renewable fuel, the method comprising:
   harvesting carbon dioxide emitted from an industrial process;
   dissociating biomass waste under an anaerobic process to produce carbon monoxide, one or more carbon donors and hydrogen, wherein the hydrogen is produced from the dissociation of the biomass waste at a remote location, the dissociating the biomass waste including:
     thermochemically producing hydrocarbons and the one or more carbon donors from the biomass waste as a transportable precursor to hydrogen at a first location where the biomass is dissociated,
     transporting in the hydrocarbons through a pipeline, and
     separating the hydrocarbons into the carbon monoxide and the hydrogen at the remote location;

generating thermochemically shifted carbon monoxide and additional hydrogen by reacting the harvested carbon dioxide with the biomass waste produced one or more carbon donors;

reacting the biomass produced carbon monoxide and the thermochemically shifted carbon monoxide with the biomass produced hydrogen and the additional hydrogen under pressure and heat to generate a renewable fuel; and converting at least a portion of the renewable fuel to a carbon-based durable good.

9. The method of claim 8, wherein the one or more carbon donors comprises at least one of hydrocarbon and alcohol.

10. The method of claim 8, wherein the renewable fuel comprises at least one of alcohol and ether.

11. The method of claim 10, wherein the alcohol comprises at least one of methanol and ethanol; and
the ether comprises dimethyl ether (DME).

12. The method of claim 11, comprising converting the DME to generate a polymer precursor to a durable good.

13. The method of claim 8, comprising adding a catalyst to enhance production of the renewable fuel wherein the catalyst comprises at least one of transition metal carbides, borides, and nitrides.

14. The method of claim 13, wherein the transition metal carbides, borides, and nitrides comprise at least one of $Fe_3C$, $Co_3C$, $Co_3Fe_3C_2$, $Mn_3C$, $FeC_3$, $CoC_3$, $CoFeC_6$, $MnFeC_6$, $Mn_5C_2$, $MnFeC_6$, $Fe_3Cr_3C_2$, $Fe_3Co_2BNC_2$, $Fe_3VC_2$, $Fe_4NC_2$, $Fe3MoC_2$, and $Fe_5BNC$.

\* \* \* \* \*